Figure 1:
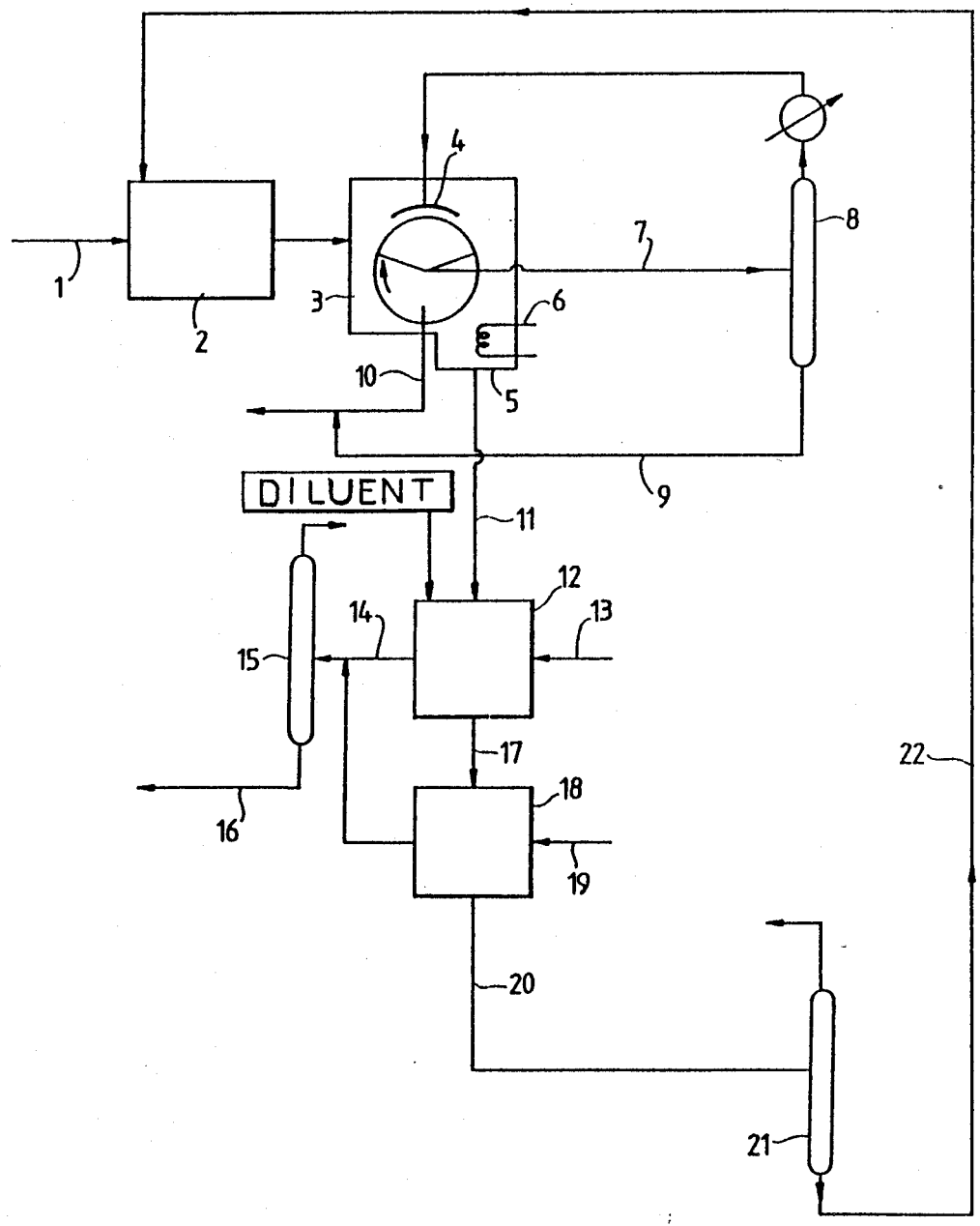

United States Patent [19]

Flett et al.

[11] Patent Number: 4,956,520
[45] Date of Patent: Sep. 11, 1990

[54] SEPARATION PROCESS

[75] Inventors: David S. Flett, Middlesbrough; John E. Lloyd, Darlington, both of England

[73] Assignee: Imperial Chemical Industries PLC, London, England

[21] Appl. No.: 106,368

[22] Filed: Oct. 9, 1987

[30] Foreign Application Priority Data

Oct. 9, 1986 [GB] United Kingdom ............. 8624266

[51] Int. Cl.$^5$ ............................................. C07C 7/14
[52] U.S. Cl. ................................... 585/815; 585/816; 585/817
[58] Field of Search .............. 585/812, 814, 815, 816, 585/817

[56] References Cited

U.S. PATENT DOCUMENTS

| | | | |
|---|---|---|---|
| 2,985,694 | 5/1961 | Talbot | 585/812 |
| 3,177,265 | 4/1965 | Lammers | 585/812 X |
| 3,462,508 | 8/1969 | Dresser et al. | 585/812 X |
| 3,462,509 | 8/1969 | Dresser et al. | 585/812 X |
| 3,487,652 | 1/1970 | McKay | 585/812 X |
| 3,916,018 | 10/1975 | Edison et al. | 585/812 X |

FOREIGN PATENT DOCUMENTS

| | | |
|---|---|---|
| 1768476 | 11/1971 | Fed. Rep. of Germany . |
| 1151606 | 5/1969 | United Kingdom ............. 585/812 |
| 1221867 | 2/1971 | United Kingdom . |

*Primary Examiner*—Glenn Caldarola
*Attorney, Agent, or Firm*—Cushman, Darby & Cushman

[57] ABSTRACT

Separation of a crystallizable component, especially paraxylene, from solution by chilling to form a slurry of crystals and liquid, separating crystals of the component in a first separator while simultaneously washing the crystals with a wash liquid and then re-melting the crystals, re-chilling them, separating the crystals in a second separator and washing them with a second wash liquid.

11 Claims, 1 Drawing Sheet

SEPARATION PROCESS

This invention relates to a separation process.

The separation of crystallisable components from solutions or slurries by chilling and separating crystals of a component in, for example, centrifuges or filters is a well-known and widely operated process. It is also known to wash such crystals with a wash liquid, which is normally chosen so as not to dissolve an excessive proportion of the crystallised component and so as to be miscible with the mother liquor from which it may be readily separable, for example by distillation.

The separation by crystallisation of para-xylene from mixtures containing it and other $C_8$ aromatic hydrocarbons is a process which is operated in several parts of the world. Various crystallisation processes have been proposed, several of which involve two crystallisation steps although some single stage crystallisation processes have also been proposed. A number of wash liquids have also been proposed, for example alcohols having one to three carbon atoms, toluene and paraffins or cycloparaffins having 4 to 6 carbon atoms, especially pentane.

Such prior art processes produce para-xylene of high purity and it is quite common now to produce para-xylene of 99% purity. As is known, one of the principal uses for para-xylene is as a feedstock for oxidation to terephthalic acid. Until quite recently, para-xylene of 99% or slightly higher purity was widely accepted by terephthalic acid producers but latterly there has been a demand for purer and purer para-xylene, preferably of at least 99.5% purity. Improving the purity of para-xylene obtained on existing para-xylene plants from say 99% to better than 99.5% has posed considerable difficulties for xylene manufacturers. However, we have now surprisingly found that it is possible to modify existing processes so as to obtain para-xylene of very high purity in an economic manner.

According to the present invention a process for the separation of a crystallisable component from a solution thereof comprises crystallising at least part of the component by chilling the solution to give a mixture of crystals and liquid, separating crystals of the component in a first separator while simultaneously washing said crystals with a first wash liquid, melting said crystals to produce a second solution of the component, chilling said solution to produce a second mixture of crystals of the component and liquid, separating crystals of the component in a second separator and washing the crystals thus obtained with a second wash liquid.

The crystals which have been washed with the second wash liquid are separated from the wash liquid in conventional fashion, for example by distilling off the wash liquid. The mother liquor from the second separator may contain appreciable, recoverable quantities of the desired crystal component and it is preferred therefore to re-chill this mother liquor, separate crystals of the component in a third separator, wash the crystals with a third wash liquid and finally separate the crystals from the third wash liquid.

It is preferred that the three wash liquids should be identical but different wash liquids may be used, if desired. However the use of different wash liquids will require facilities to separate them one from another, thereby adding to the costs of the separation process of the invention. The wash liquid(s) may be any of those conventionally used in crystallisation processes of this kind.

The process of this invention is particularly appropriate to the separation of para-xylene from mixtures thereof with at least one other xylene and/or ethylbenzene. Thus solutions suitable for treatment in the process of the invention may comprise for example from 8 to 35%, preferably 16 to 25% by weight of para-xylene. In the separation of para-xylene, suitable wash liquids include for example alcohols having 1 to 3 carbon atoms, especially methanol, paraffins or cycloparaffins having 4 to 6 carbon atoms, especially pentane, and aromatic hydrocarbons, for example toluene.

In the preferred embodiment of the process of this invention, the incoming feedstock of xylenes and/or ethylbenzene is chilled so that its temperature is reduced to a temperature of the order of $-60°$ C. or $-70°$ C. The first and second separators for separating chilled crystals may comprise for example filters or centrifuges. The wash liquid added in the first separator may be added at a temperature which is suitably in the range of $+20°$ C. down to $-70°$ C. The amount of wash liquid which is required will depend to some extent on the composition of the initial feedstock. In general, however, it is preferred to use amounts in the range 0.05 to 0.5 parts weight wash liquid/part weight of crystal cake, more preferably 0.05 to 0.13 parts weight wash liquid/part weight crystal cake.

One embodiment of the invention will now be described with reference to FIG. 1 which illustrates a simplified flow-sheet of a plant for operating the process of the invention.

A feedstock which is a mixture of xylenes and ethyl benzene of composition 22% para-xylene, 47% meta-xylene, 21% ortho-xylene and 4% ethyl benzene and 6% of other, mainly aromatic, components by weight is fed (line (1)) to chillers (2) and cooled to about $-66°$ C., to produce a slurry containing about 15% by weight solids. The slurry is separated in a filter 3 and the crystals are simultaneously washed with pentane wash liquid fed through pipe 4 at a temperature of about 10° C.

The crystals are passed through a melt tank 5 provided with a heater 6 to form a solution containing about 87% by weight paraxylene, about 8% pentane and some other minor components. At the same time, pentane-contaminated washings are taken from the filter along line 7 to a distillation zone 8 where pentane is removed overhead for recycle, after re-chilling if necessary, to the filter 3. Bottoms from the distillation zone is passed along line 9 and combined with the pentane-free filtrate (line (10)) from the filter. The combined stream, containing about 9% para-xylene, is recycled to a xylenes isomerisation plant (not shown). Removal of the pentane-contaminated washings along line 7 greatly assists in keeping the combined isomeriser recycle stream free of pentane.

The solution containing 87% para-xylene is fed via line 11 to a further chilling and separation zone 12. The crystals formed therein are washed with pentane fed along line 13. The ratio of pentane to crystal cake is similar to that used in filter 3. The Applicants have found that para-xylene recovery is assisted by the optional addition of a diluent to zone 12. The diluent may be any suitable inert liquid but in the present example it is particularly convenient to add further pentane to act as said diluent. A stream of washed crystals and pentane is removed from zone 12 via line 14 to a distillation zone 15 where pentane is removed overhead and very pure para-xylene (at least 99.5% pure) is removed as the bottoms product (line 16). A mother liquor from the zone 12, which may contain of the order of 45% by weight para-xylene, is fed via line 17 for further chilling and separation in a so-called recycle zone 18. The crystals obtained are again washed with pentane fed by line 19 and the washed crystals (and some pentane) are removed and combined with the similar stream in line 14. The ratio of pentane to crystal cake used in zone 18 is conveniently similar to that employed in zone 12.

Mother liquor from zone 18 containing about 30% by weight of para-xylene is fed via line 20 to a distillation zone 21 where pentane is removed overhead and the bottoms xylenes stream recycled via line 22 to chillers 2.

The above description of the process of this invention has been somewhat simplified for ease of understanding. Those skilled in this art will readily understand that additional facilities such as heat exchangers are provided where necessary to improve the thermodynamic efficiency of the plant.

The following more specific examples further illustrate the process of this invention. Table 1 below summarises the para-xylene content of a feedstock to the first chilling zone (2) (see FIG. 1), the para-xylene content of the filter cake prior to washing with Pentane, the para-xylene content and $C_5$ hydrocarbon content of the cake after washing and the para-xylene content of the depentanised cake. The wash ratio defined as tonnes wash liquid/tonnes cake is also given. All percentages are by weight

TABLE 1

|  | Run 1 | Run 2 |
|---|---|---|
| % paraxylene |  |  |
| (a) feedstock | 24.4 | 24.3 |
| (b) initial cake, pre-wash | 74.1 | 74.3 |
| (c) washed cake | 77.2 | 86.2 |
| ($C_5$ hydrocarbon content) | (3.7) | (8.8) |
| (d) pentane-free cake | 80.2 | 94.5 |
| Wash Ratio | 0.05 | 0.23 |

Table 2 below gives results of further runs in which washed and melted cake from the first chilling and separation was fed to the second chilling and separation zone (12), pentane being added as a diluent to this zone. The chilling temperature was in the range of $-7$ to $-15°$ C. and the feed rate of the melted cake+diluent ranged from an initial 4 parts by weight per hour to a final 9½ parts by weight per hour, the increase in rate occurring stepwise gradually through the runs. The chilled cake was washed with pentane, the pentane wash rate being 0.33 parts by weight per hour. Table 2 summarises the feed and depentanised product analyses (all % w/w) for two runs.

TABLE 2

|  | Run 1 | | Run 2 | |
|---|---|---|---|---|
|  | Feed Analysis | Product Analysis | Feed Analysis | Product Analysis |
| Pentane | 19.24 | 0.01 | 22.70 | 0.15 |
| Para-Xylene | 75.16 | 99.87 | 71.74 | 99.73 |
| Meta-Xylene | 3.55 | 0.06 | 3.47 | 0.08 |
| Ortho-Xylene | 1.5 | 0.03 | 1.49 | 0.03 |

TABLE 2-continued

|  | Run 1 | | Run 2 | |
|---|---|---|---|---|
|  | Feed Analysis | Product Analysis | Feed Analysis | Product Analysis |
| Benzene | 0.02 | 0.006 | 0.02 | <0.01 |
| Toluene | 0.17 | 0.011 | 0.11 | 0.01 |
| Ethylbenzene | 0.13 | <0.01 | 0.12 | <0.01 |
| Non-aromatics | 0.01 | <0.01 | 0.01 | <0.01 |
| > C8 $C_8$ Ends | 0.14 | <0.01 | 0.11 | <0.01 |

The improved process of this invention produces para-xylene which has a purity of at least 99.5% and typically of 99.7% or 99.8%. Although such an improvement in purity over that obtainable in existing plants (99.0 to 99.5%) may seem small, the economic advantages are considerable in large-scale plants having capacities which may range up to 300,000 tons per annum or even more. Moreover the provision of even purer para-xylene than hitherto also means that downstream producers, such as terephthalic acid manufacturers, can improve the purity of their products and the efficiencies of their plants.

We claim:

1. A process for the separation of a crystallisable component from a solution thereof which comprises crystallising at least part of the component by chilling the solution to give a mixture of crystals and liquid, separating crystals of the component in a first separator while simultaneously washing said crystals with a first wash liquid, melting said crystals to produce a second solution of the component, chilling said solution to produce a second mixture of crystals of the component and liquid, separating crystals of the component in a second separator and washing the crystals thus obtained with a second wash liquid.

2. A process as claimed in claim 1 in which mother liquor from said second separator is re-chilled to form further crystals of the crystallisable components, the crystals are separated in a third separator, washed with a third wash liquid and thereafter separated from the wash liquid.

3. A process as claimed in claim 1 in which an inert liquid diluent is added to the said second solution of the crystallisable component before separation of said crystals.

4. A process as claimed in claim 1 in which the wash liquids used are identical.

5. A process as claimed in claim 3 in which the inert liquid diluent is identical to the second wash liquid.

6. A process as claimed in claim 4 in which the wash liquids are selected from alcohols having 1 to 3 carbon atoms, paraffins and cycloparaffins having 4 to 6 carbon atoms, and aromatic hydrocarbons.

7. A process as claimed in claim 6 in which the wash liquids are selected from methanol, pentane and toluene.

8. A process as claimed in claim 1 in which the crystallisable component to be separated is para-xylene from its admixture with at least one other xylene isomer and-/or ethylbenzene.

9. A process as claimed in claim 8 in which the feedstock to the process comprises 8 to 35% by weight of para-xylene.

10. Para-xylene having a purity of at least 99.5% whenever produced by a process according to any one of claims 1 to 9 or 11.

11. A process as claimed in claim 2 in which the wash liquids used are identical.

* * * * *